United States Patent
Morse

[19]

[11] Patent Number: 6,056,720
[45] Date of Patent: May 2, 2000

[54] OCCLUSION CANNULA AND METHODS OF USE

[75] Inventor: Stephen A Morse, Palo Alto, Calif.

[73] Assignee: Embol-X, Inc., Mountain View, Calif.

[21] Appl. No.: 09/198,439

[22] Filed: Nov. 24, 1998

[51] Int. Cl.⁷ .................................................. A61M 29/00
[52] U.S. Cl. ................... 604/96; 604/96; 606/191
[58] Field of Search ............... 604/96–101, 174, 604/177, 507, 508, 509; 606/85, 191, 192, 194

[56] References Cited

U.S. PATENT DOCUMENTS

| | | | |
|---|---|---|---|
| 2,687,131 | 8/1954 | Raiche | 128/349 |
| 3,811,448 | 5/1974 | Morton | 128/349 |
| 4,610,662 | 9/1986 | Weikl et al. | 604/53 |
| 5,151,087 | 9/1992 | Jonkman | 604/164 |
| 5,312,344 | 5/1994 | Grinfeld et al. | 604/101 |
| 5,330,451 | 7/1994 | Gabbay | 604/284 |
| 5,330,498 | 7/1994 | Hill | 606/194 |
| 5,425,708 | 6/1995 | Nasu | 604/96 |
| 5,478,309 | 12/1995 | Sweezer et al. | 604/4 |
| 5,599,329 | 2/1997 | Gabbay | 604/284 |

FOREIGN PATENT DOCUMENTS 0218275  4/1987  European Pat. Off. .

*Primary Examiner*—Wynn Wood Coggins
*Assistant Examiner*—Kevin C. Sirmons
*Attorney, Agent, or Firm*—Lyon & Lyon LLP

[57] ABSTRACT

The invention provides a nested tubing cannula which comprises outer and inner elongate tubular members, each having a proximal end, a distal end, and a lumen therebetween. The inner tubular member is sealed at its distal end and is nested substantially coaxially within the lumen of the outer tubular member, so that the gap between the inner and the outer tubular member defines a second lumen whereas the first lumen is the lumen of the inner tubular member. A tubular sleeve is disposed coaxially between the inner and outer tubular members. A balloon is mounted on a distal region of the outer tubular member and is in communication with the first lumen. The cannula further comprises a port proximal or distal the balloon occluder and is in communication with the second lumen. Methods for making the devices herein are disclosed.

22 Claims, 1 Drawing Sheet

OCCLUSION CANNULA AND METHODS OF USE

FIELD OF THE INVENTION

This invention relates to methods and apparatus for administering cardioplegia to the aorta during cardiac surgery. The devices include an occlusion cannula that can include various features such as a cutting blade, a blade guard, a flange, radiopaque markers and an occluder aligner to properly position the distal end of the device within the aorta. Once the occlusion cannula is in its proper position, the occluder is expanded to occlude the aorta downstream of the infusion port and cardioplegia solution is then introduced through the infusion port to arrest the heart. The infusion port can alternately be used to aspirate cardioplegia or embolic debris or other unwanted material from the aorta.

BACKGROUND OF THE INVENTION

Currently, the most common method of temporarily occluding the ascending aorta and arresting the heart during open-heart surgery utilizes a mechanical cross clamp and a cardioplegia cannula. Once the chest cavity has been opened, access to the heart and to the adjacent vessels is provided. The ascending aorta is partially dissected from the surrounding tissue and exposed. Arterial and venous cannulas are inserted and sutured into place. The cannulas are connected to the cardiopulmonary bypass machine, and bypass blood oxygenation is established.

At this point, the heart must be arrested and isolated from the rest of the circulatory system. A mechanical cross clamp is positioned between the cardioplegia cannula and the aortic cannula and is actuated. The aorta is completely collapsed at the clamp site, thus stopping flow of blood between the coronary arteries and the innominate artery, and the oxygenated bypass blood is shunted around the heart. Once the vessel occlusion has been completed, cardioplegia solution is introduced through the cardioplegia cannula to arrest the heart. The surgeon may now proceed with the desired operation.

Other less common means of occluding the aorta include percutaneous balloon catheter occlusion, direct aortic balloon catheter (Foley) occlusion, aortic balloon catheter occlusion, and an inflating diaphragm occluder (Hill—occlusion trocar). The percutaneous balloon catheter is inserted typically from the femoral artery feed through the descending aorta, across the aortic arch into position in the ascending aorta. Once in the ascending aorta, the balloon occluder is inflated and flow stopped.

As a simple replacement for the mechanical cross clamp, a Foley catheter may be placed through an additional incision site near the standard cross clamp site. Once inserted, the Foley catheter balloon is inflated and flow is stopped. Similarly, an aortic balloon catheter is placed directly into the aorta. This catheter replaces the standard aortic cannula by delivering the cardiopulmonary bypass (CPB) blood back to the arterial circulatory system. The occluder balloon is located on the catheter proximal to CPB blood exit port on the cannula. The occlusion trocar is desired to offer similar features as the aortic balloon occluder cannula and would be used in place of the standard aortic cannula. However, it relies on an inflatable diaphragm to occlude the vessel.

The use of a balloon to occlude an artery has been disclosed by Gabbay, U.S. Pat. No. 5,330,451 (this and all other references cited herein are expressly incorporated by reference as if fully set forth in their entirety herein). The Gabbay device included a perfusion cannula having a proximal balloon occluder and a distal intra—aortic balloon to divert blood to the carotid arteries. The Gabbay perfusion cannula is disclosed for use during open-heart surgery in order to prevent complications associated therewith.

Moreover, Peters, U.S. Pat. No. 5,433,700, discusses a method for inducing cardioplegic arrest using an arterial balloon catheter to occlude the ascending aorta. The Peters method includes the steps of maintaining systemic circulation using peripheral cardiopulmonary bypass, venting the left side of the heart, and introducing a cardioplegic agent into the coronary circulation. This procedure is said to prepare the heart for a variety of surgical procedures. Disclosures of similar endovascular occlusion catheters can be found in Machold et al., U.S. Pat. No. 5,458,574, Stevens, International Application No. PCT/US93/12323, Stevens et al., International Application No. PCT/US94/12986, Nasu, U.S. Pat. No. 5,425,708 and Grinfeld et al., U.S. Pat. No. 5,312,344.

Each of the existing methods of blocking aortic blood flow and arresting the heart carries with it some undesired aspects. The mechanical cross clamp offers simplicity and reliably consistent operation. However, the physical clamping action on the vessel has been linked to many adverse body responses. Barbut et al. ("Cerebral Emboli Detected During Bypass Surgery Are Associated With Clamp Removal," Stroke, 25(12):2398–2402 (1994), incorporated herein by reference in its entirety) noted the majority of embolic events (release) is associated with the actuation and release of the cross clamp during coronary bypass graft surgery. The clamping action may be responsible for breaking up and freeing atherosclerotic buildup on the vessel walls. In addition, the potential for vascular damage, like aortic dissections, may also incur during the clamp application.

The percutaneous balloon catheter occluder has a distinct drawback in that it must be placed with visionary assistance. Fluoroscopy is typically used to position the device in the aorta. This added equipment is not always readily available in the surgical suite. In addition, the catheter placement up to the aorta may also create additional vascular trauma and emboli generation.

The use of a Foley catheter to occlude the aorta requires an additional incision site to place the device. The extra cut is an additional insult site and requires sutures to close. Generation of emboli and the potential of aortic dissection directly associated with just the incision may potentially outweigh the benefits of using the catheter.

The aortic balloon occluder cannula addresses many of the deficiencies of the previous devices. Placement is easy to visualize, no extra cuts are required, and there is no need for the potentially traumatic cross clamp. However the currently—available aortic balloon occluders suffer from problems of migration within the ascending aorta because the cannulas on which the balloons are mounted are typically flexible tubes as disclosed by Grinfeld et al. and Nasu. Attempts to solve the migration problem include balloon designs with a large "footprint" in the distal region of the cannula. (See Nasu, supra.) This large footprint balloon is a less than adequate solution because it encroaches into the already limited area of the ascending aorta in which surgical access is available. Further, use of each of these aortic occluding balloons requires a cardioplegia cannula to be inserted through an additional incision site to arrest the heart.

A need exists for an aortic cannula having both a balloon occluder which can isolate the ascending aorta from peripheral vasculature without substantial migration of the occluder into the ascending aorta, thereby reducing or eliminating the need for aortic cross—clamping, and an associated cardioplegia infusion port which eliminates the need for a separate incision for a cardioplegia cannula. Existing devices are inadequate for this purpose.

SUMMARY OF THE INVENTION

The present invention relates to medical devices and their methods of use, and particularly occlusion cannula. The occlusion cannula comprises a cannula having an occluder to isolate the ascending aorta from peripheral vasculature during cardiac surgery and an infusion port for administering cardioplegia to arrest the heart. The infusion port can alternately be used to aspirate cardioplegia or embolic debris or other unwanted material from the aorta. The devices of the present invention may include various features such as a cutting blade, a blade guard, a flange, radiopaque markers and an occluder aligner to properly position the distal end of the device within the aorta.

In one embodiment, the device includes a substantially rigid cannula adapted to enter the aorta with a proximal end that receives cardioplegia solution into a cardioplegia lumen and delivers it to an infusion port in the distal region of the cannula. An occluder, mounted on the distal region of the cannula, expands away from the cannula upon activation to substantially occlude the aorta downstream from the infusion port. During use, the occluder isolates the ascending aorta from the peripheral vasculature. The substantially rigid nature of the cannula inhibits migration of the occluder into the ascending aorta, thus overcoming problems associated with other currently available aortic balloon cannulas.

An alternative embodiment of an occlusion cannula may comprise a rigid, preformed elongate tubular member having a proximal end, a distal region, a distal end, and a lumen extending from the proximal end to a perfusion port in the distal region. This lumen and port can be used to deliver cardioplegia. The distal region includes three segments. The first segment is angled from the axis of the proximal tubular member. The second segment curves in a direction opposite from the first segment. The third segment is substantially linear and lies at approximately a 90—degree angle to the axis of the proximal tubular member. The curved second segment has two beneficial properties. First, it inhibits migration of the occluder into the ascending aorta. Second, the curved segment brings the balloon into closer proximity to the proximal tubular member, and thereby improves stability of the occluder in use. In certain embodiments, the tubular member includes another lumen which extends distally and communicates with a port adjacent the distal region for measuring blood pressure.

In certain embodiments, the occluder is an inflatable balloon. In other embodiments, the occluder is a foam-filled, self-expanding balloon. Certain balloon embodiments also include a lumen which can be used to inflate the balloon or alternately can be used to apply negative pressure to deflate the balloon. Other embodiments include an aspiration lumen which terminates at the infusion port so that the infusion port can alternately be used to deliver cardioplegia solution or aspirate embolic debris and other unwanted material from the aorta. Another embodiment further includes an occluder aligner to help position the distal end of the cannula within the aorta and to stabilize the position of the occluder during expansion. In another embodiment, the device includes a cannula associated with a cutting blade which is adapted to cut through the wall of the aorta to allow introduction of the cannula. The proximal end of the cannula is adapted to receive cardioplegia solution into a cardioplegia lumen and deliver it to an infusion port in the distal region of the cannula. An occluder mounted on the distal region of the cannula expands away from the cannula upon activation to substantially occlude the aorta downstream from the infusion port. During use, the occluder isolates the ascending aorta from the peripheral vasculature. Certain embodiments also include a blade guard which moves when pressed against the aorta to allow the blade to cut through the wall of the aorta and then repositions to prevent the blade from cutting. Other embodiments further include an occluder aligner, a lumen which can be used to inflate the or deflate the balloon or an aspiration lumen which terminates with the infusion port. For more detailed descriptions of the construction of a cardioplegia occluder, the reader is referred to Tsugita et. al., U.S. application Ser. No. 08/993,202, filed Dec. 18, 1997, incorporated herein by reference.

The methods of the present invention include administering cardioplegia to the aorta during cardiac surgery using a occlusion cannula as described above. An incision is made in the aorta, and the distal end of the cannula is inserted through the incision. The occluder is expanded to occlude the aorta and thereby isolate the ascending aorta from peripheral circulation without substantial migration of the occluder within the ascending aorta. Cardioplegia solution may be infused through the infusion port to arrest the heart. In embodiments that include a cutting blade, the step of making the incision in the aorta is performed by the cutting blade. In embodiments that include an aspiration lumen, the method further includes the step of aspirating cardioplegia and embolic debris from the aorta by applying negative pressure to the aspiration lumen.

DETAILED DESCRIPTION

Figure 1:
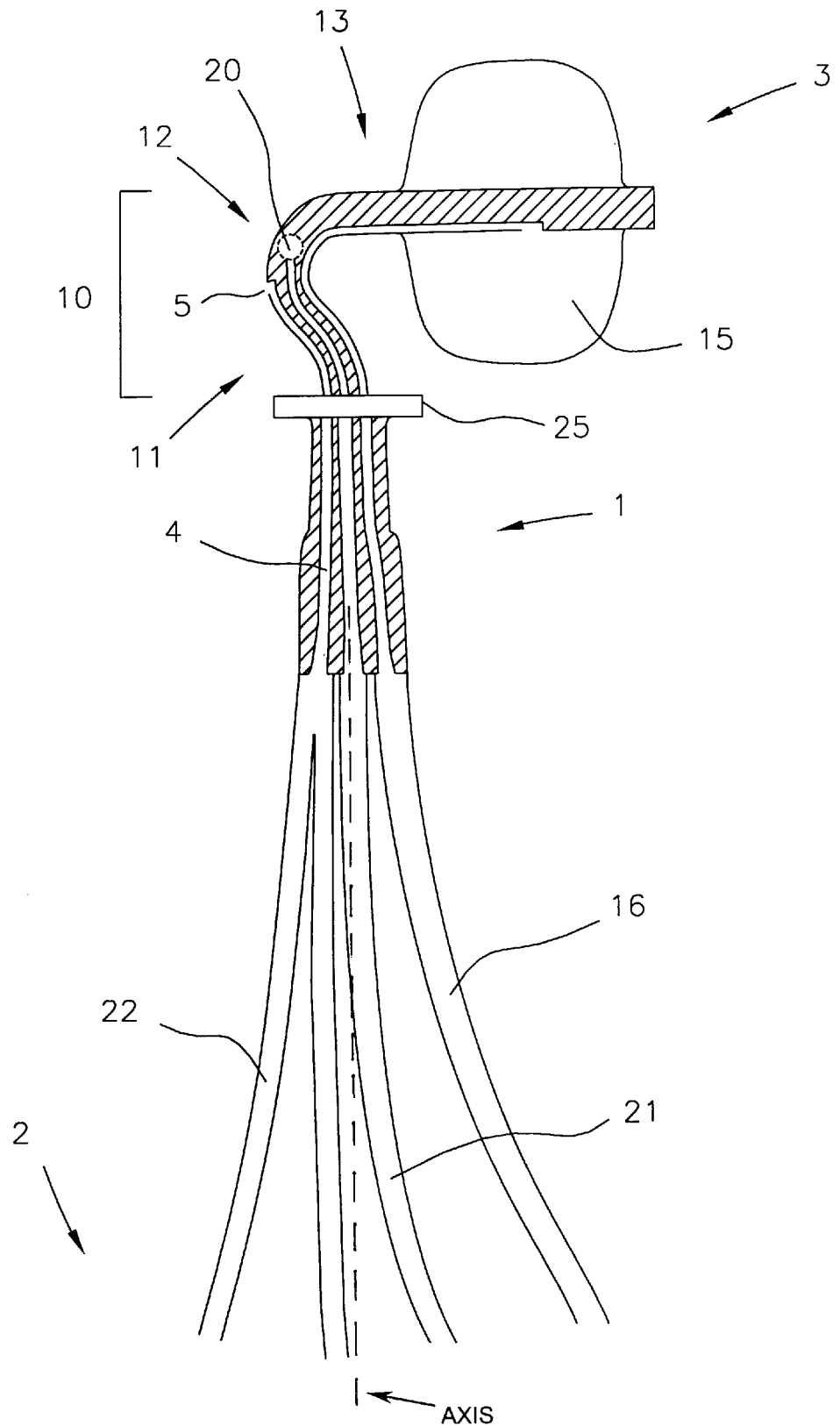
FIG. 1 depicts an occlusion cannula according to the invention, having an angled distal segment.

Referring more to the figure, FIG. 1 depicts an embodiment of an occlusion cannula having an angled distal segment. Tubular member 1 comprises proximal end 2, distal end 3, distal region 10, and lumen 4. Lumen 4 extends from proximal end 2 to perfusion port 5 in the distal region. Perfusion port 5 may be a cardioplegia port. Distal region 10 is composed of a substantially rigid preformed material which resists bending under the forces encountered under the differential in blood pressure during cardiopulmonary bypass in the aorta. Region 10 includes three segments. First segment 11 is angled from the axis of the proximal tubular member. Second segment 12 curves in a direction opposite from first segment 11. Third segment 13 is substantially linear and lies at approximately a 90—degree angle to the axis of the proximal tubular member. The curved segment further inhibits migration of the occlusion cannula in the ascending aorta. Balloon occluder 15, which may comprise an elastomeric balloon, is mounted on third segment 13, distal to perfusion port 5. Balloon inflation lumen 16, communicating with balloon occluder 15, extends proximal from the distal region. The elongate member may further comprise suture flange 25. Aspiration lumen 22, extending distally and communicating with perfusion port 5, can be used to aspirate embolic debris and other unwanted material from the aorta. Lumen 21, which extends distally and communicates with port 20, can be used for measuring blood pressure.

In using the occlusion cannula described above for cannulation of a patient's blood vessel, the cannula is first inserted into a blood vessel, which may be an artery such as an aorta. The cannula may be inserted through an incision in open-heart surgeries or through a port-access in minimally invasive surgeries. The cannula may be secured onto the blood vessel by placing sutures between suture flange 25 and the outer blood vessel wall. During coronary artery bypass or heart valve repair surgery, for example, balloon occluder 15 is inflated through inflation lumen 16 to provide isolation of coronary circulation from the peripheral circulation for cardiopulmonary bypass. Cardioplegia solution can then be infused through lumen 4 and port 5 upstream the ascending aorta to arrest the heart. During cardiopulmonary bypass, the differential pressure gradient across the cannula tends to cause a traditional cannula to migrate upstream the ascending aorta. The curved distal segment of this occlusion cannula is better adapted to withstand the higher pressure downstream the aorta, thereby minimizing migration of the cannula. Blood pressure upstream the aorta may be monitored by a blood pressure monitoring device through port 20 and lumen 21. Embolic materials, such as calcium, tissue debris, atheromatous plaque, and air may be aspirated through port 5 and lumen 22.

The length of an occlusion cannula will generally be between 5 and 15 inches, preferably approximately 8 inches. The length of the first segment in the distal region will generally be between 0.1 and 0.8 inches, preferably approximately 0.3 inches. The length of the segment in the distal region will generally be between 0.1 and 0.5 inches, preferably approximately 0.2 inches. The length of the third segment in the distal region will generally be between 0.2 and 0.8 inches, preferably approximately 0.4 inches. The outer diameter of an occlusion cannula lumen will generally be between 0.02 and 0.2 inches, preferably approximately 0.1 inches.

The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claims.

What is claimed is:

1. An occlusion cannula comprising:
    a rigid, preformed elongate tubular member having a proximal end, a distal region, a distal end, and a lumen extending from the proximal end to a perfusion port in the distal region, the distal region having a first segment curved from an axis of the proximal tubular member, a second segment which curves in a direction opposite from the first segment, and a third segment which is substantially linear and lies at approximately a 90-degree angle to the axis of the proximal tubular member;
    and a balloon occluder mounted on the third segment of the distal region, distal the perfusion port, the balloon occluder having an inflation lumen which extends proximal from the distal region.

2. The occlusion cannula of claim 1, wherein the tubular member further comprises a lumen which extends distally and communicates with a port for measuring blood pressure adjacent the distal region.

3. The occlusion cannula of claim 1, further comprising a suture flange mounted on the tubular member.

4. The occlusion cannula of claim 1, wherein the tubular member further comprises an aspiration lumen which extends distally and communicates with the perfusion port.

5. The occlusion cannula of claim 1, wherein the balloon occluder comprises an elastomeric balloon.

6. The occlusion cannula of claim 1, wherein the perfusion port is a cardioplegia port.

7. The occlusion cannula of claim 1, further comprising a cutting blade.

8. The occlusion cannula of claim 1, wherein the cutting blade further includes a blade guard which slideably receives the cutting blade and moves when pressed against a vessel to allow the blade to cut through the wall of the vessel and then repositions to prevent the blade from cutting.

9. A method of cannulation of a patient's blood vessel, comprising the steps of:
    providing an occlusion cannula comprising an elongate tubular member having a proximal end, a distal region, a distal end, and a lumen extending from the proximal end to a perfusion port in the distal region, the distal region having a first segment angled from the axis of the proximal tubular member, a second segment which curves in a direction opposite from the first segment, and a third segment which is substantially linear and lies at approximately a 90 degree angle to the axis of the proximal tubular member, and a balloon occluder mounted on the third segment of the distal region, distal the perfusion port, the balloon occluder having an inflation lumen which extends proximal from the distal region;
    inserting the occlusion cannula into a blood vessel;
    inflating the balloon occluder; and
    infusing fluid through the lumen of the cannula into the blood vessel.

10. The method of claim 9, wherein the blood vessel is an artery.

11. The method of claim 10, wherein the artery is the aorta.

12. The method of claim 11, further comprising the step of heat bending the distal end of the inner and outer tubular members so that the distal end is angulated relative to the proximal end.

13. The method of claim 12, further comprising the step of placing sutures between the suture flange and the blood vessel.

14. The method of claim 11, further comprising a step of creating a channel through the outer tubular member, said channel in communication with the lumen disposed between the inner and outer tubular members.

15. The method of claim 11, further comprising the step of mounting an elastomeric balloon on the distal end of the outer tubular member.

16. The method of claim 9, wherein the tubular member further comprises an aspiration lumen which extends distally and communicates with the perfusion port.

17. The method of claim 16, further comprising the step of aspirating any one of fluid, blood, emboli, tissue debris, and air through the perfusion port.

18. The method of claim 9, wherein the occlusion cannula is inserted through a port-access.

19. The method of claim 9, wherein the fluid is cardioplegia solution.

20. The method of claim 9, further comprising the step of performing cardiopulmonary bypass.

21. The method of claim 9, further comprising the step of performing coronary artery bypass graft surgery.

22. The method of claim 9, further comprising the step of performing valve repair surgery.

* * * * *